(12) United States Patent  (10) Patent No.: US 8,060,376 B2
Horner  (45) Date of Patent: Nov. 15, 2011

(54) SYSTEM AND METHOD FOR COLLECTION OF COMMUNITY HEALTH AND ADMINISTRATIVE DATA

(75) Inventor: Douglas R. Horner, Fort Wayne, IN (US)

(73) Assignee: NoMoreClipBoard, LLC, Fort Wayne, IN (US)

( * ) Notice: Subject to any disclaimer, the term of this patent is extended or adjusted under 35 U.S.C. 154(b) by 1768 days.

(21) Appl. No.: 10/957,491

(22) Filed: Oct. 1, 2004

(65) Prior Publication Data

US 2006/0074719 A1   Apr. 6, 2006

(51) Int. Cl.
*G06Q 10/00* (2006.01)
*G06F 19/00* (2011.01)
(52) U.S. Cl. ............................................. 705/2; 705/3
(58) Field of Classification Search ................. 705/2–3; 600/300; 707/201; 709/203
See application file for complete search history.

(56) References Cited

U.S. PATENT DOCUMENTS

| | | | |
|---|---|---|---|
| 5,664,109 A | | 9/1997 | Johnson et al. |
| 5,772,585 A * | | 6/1998 | Lavin et al. ................... 600/300 |
| 5,924,074 A | | 7/1999 | Evans |
| 6,263,330 B1 | | 7/2001 | Bessette |
| 6,278,999 B1 | | 8/2001 | Knapp |
| 6,347,329 B1 | | 2/2002 | Evans |
| 6,757,898 B1 * | | 6/2004 | Ilsen et al. ................... 709/203 |
| 2001/0041991 A1 * | | 11/2001 | Segal et al. ................... 705/3 |
| 2002/0016721 A1 | | 2/2002 | Mason et al. |
| 2002/0016923 A1 | | 2/2002 | Knaus et al. |
| 2002/0103675 A1 | | 8/2002 | Vanelli |
| 2002/0123909 A1 | | 9/2002 | Salisbury |
| 2002/0138306 A1 | | 9/2002 | Sabovich |
| 2002/0169637 A1 | | 11/2002 | Akers et al. |
| 2002/0194029 A1 | | 12/2002 | Guan et al. |
| 2003/0023461 A1 | | 1/2003 | Quintanilla et al. |
| 2003/0040940 A1 | | 2/2003 | Nehammer |
| 2003/0088440 A1 | | 5/2003 | Dunn |
| 2003/0120516 A1 | | 6/2003 | Perednia |
| 2003/0130873 A1 | | 7/2003 | Nevin et al. |
| 2004/0034550 A1 * | | 2/2004 | Menschik et al. ................. 705/3 |
| 2004/0039757 A1 * | | 2/2004 | McClure ....................... 707/201 |
| 2006/0149594 A1 * | | 7/2006 | Hilligoss et al. .................. 705/2 |

OTHER PUBLICATIONS

Materials from Archive.org for nomoreclipboard.com; Aug. 24, 2003 or earlier.

* cited by examiner

*Primary Examiner* — Luke Gilligan
*Assistant Examiner* — Joseph Burgess
(74) *Attorney, Agent, or Firm* — Barnes & Thornburg LLP

(57) ABSTRACT

The present invention involves a health care patient document system and method which enable patients to enter clinical, administrative, and financial information normally completed on a clipboard in a medical office into a computerized system that stores the information. The patient is then enabled to direct the stored information to any health care provider whether the provider is enabled to receive the data electronically or not. For those provider clinicians and organizations not enabled to receive the information electronically, the system completes the paper-based forms already in use within the organization and sends the completed form by facsimile or mail delivery.

9 Claims, 5 Drawing Sheets

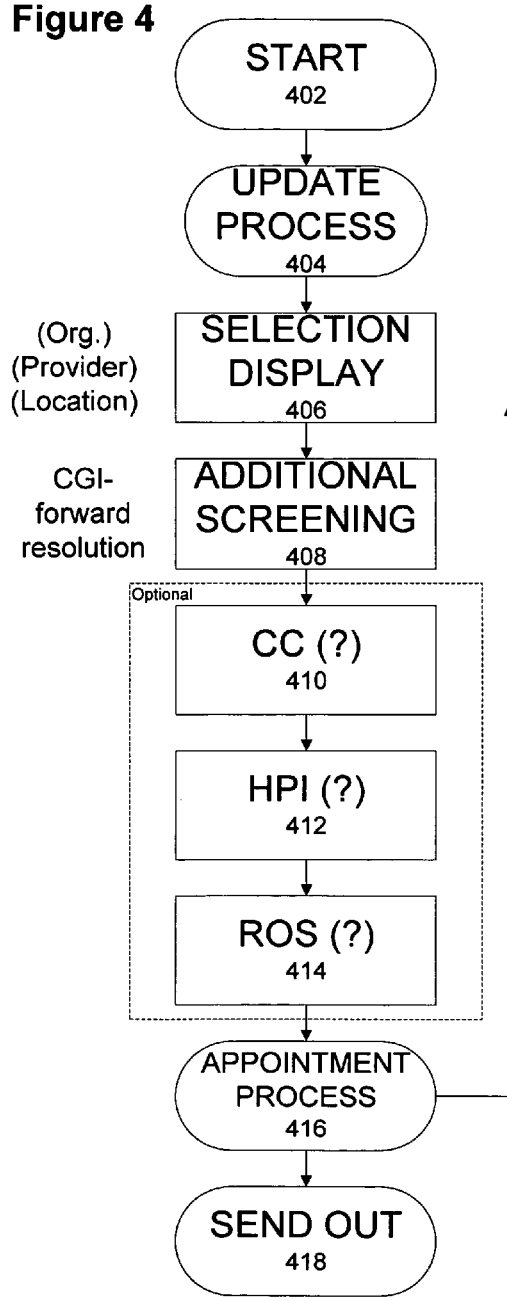
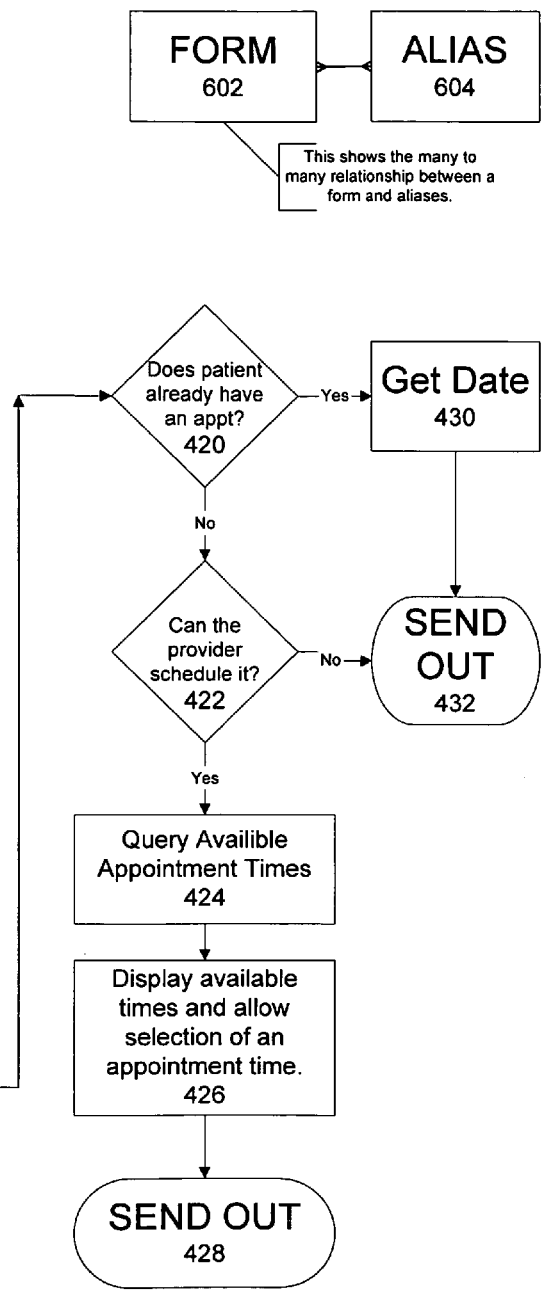

ary patterns in the community. Patients are not forced to ## SYSTEM AND METHOD FOR COLLECTION OF COMMUNITY HEALTH AND ADMINISTRATIVE DATA

BACKGROUND OF THE INVENTION

1. Field of the Invention

The invention relates to health care/medical information software. More specifically, the field of the invention is that of health care/medical information software for patient information in health care systems.

2. Description of the Related Art

Much time and many resources are spent by health care institutions and medical service practitioners, such organizations being referred to herein as "providers," collecting and re-collecting medical information from patients. Because providers have different requirements and workflow procedures based on specialty, specialized forms are in use in separate offices. Patients are forced to answer common administrative, financial, and health related questions repeatedly, typically in the format of a predefined paper form with spaces for hand written responses, as they move from provider to provider over the course of care.

Standardization of paper based forms for collecting health information have proven to be useful within an organization, but providers across a community tend to have difficulty coming to a consensus for standardization. The lack of consensus stems from differences in types and resolution of health information specialists collect, in particular health care institutions such as insurance companies and hospitals may have differing types of relevant information, as do hospitals, testing labs, and physicians. Also, the workflow within those organizations dictates the need for specialized forms and therefore requires those organizations to manually transfer information from standard forms to their custom forms.

The reason there has not been a wide spread adoption of uniform health care patient forms is that standardized forms fail to satisfy the diverse needs across the health care and medical community and there is no standard for collecting electronic health information and distributing it to every participant that require such information. Even those providers which have electronic systems have different vendors that are expecting the data in different formats, thus making it difficult to share patient information electronically. Attempts to allow patients enter their information into electronic systems using web-based questionnaires have had some success for individual organizations, but from the patient perspective this algorithm is just marginally better than the paper based process, making the patient have to fill out all the information repeatedly on different websites instead of on different clipboards.

A patient based medical/health care information system must be an elective process initiated by the patient and must insure compliance with HIPAA and other privacy legislation and concerns.

SUMMARY OF THE INVENTION

The present invention is a patient entry health care/medical information system and method which allows for patient entry to a single data repository which is compatible with all of the community's health care and medical systems, whether computer or paper based. The present invention includes profiling the various health care/medical information system entry forms (typically in paper form), determining the contents of a single database that can provide relevant patient information for all of those forms, and generating a library of forms for each health care/medical institution that can include the relevant patient information in a form compatible with the institution's current system (typically in paper form).

A third party service provider (TPS), not directly engaged in providing health care services or directing patient referrals, oversees and manages the system to ensure that providers are not skeptical of either participating and/or promoting the system. Each provider in the community is sent a letter asking them to send in blank copies of all the clipboard paperwork they have patients complete. The TPS provider then scans the clipboard paperwork sent in by the providers and constructs a database of the form image, the form type, the questions on the form, the details of the questions, the position on the form where the answers should be rendered (written), and how and where to send completed forms (i.e. fax/mail). If the provider is capable of processing information electronically the format and protocol for that physician is stored (i.e.: e-mail, h17, XML, etc) and the nomenclature of the electronic information (CPT/ICD9, NDDF, MediSpan, NDC, SNOMED, etc).

As many forms are received from the providers and entered into the system of the present invention, the software will recommend and physician reviewers will confirm a quorum of questions that are common to most of the forms. This quorum of questions in the database becomes the questionnaire that patients will fill out online. This provides the biggest return for the patient since they will only be asked questions once at registration but the information could be used to populate the forms of any of the providers in the database.

A patient visits the website to register with a username and a password that is assigned to an account. The patient completes the web-based questionnaire by answering the questions and the responses are coded and stored associated to their account. The patient's username and password are required to view and/or edit their information. No one except that patient should be able to access the information in the account from the website. As patients need to send information to different providers, they would log into the website, update the information if any changes are necessary, and then select the physician they are to see soon. The system may also prompt for additional questions that are not part of the basic questionnaire and are specific to the physician and the physician's office clipboard form (or other provider). The system then stores the final responses, and populates the physician's clipboard forms with the patient information in the format specific for the physician and sends the forms to the physician's office. It is also possible to allow patients to elect to allow providers to update their medical information on the website, although it is not necessary that providers have this capacity.

The system of the present invention is a solution that allows patients to enter their information once and electively send that information to any provider they wish. The system of the present invention formats the information for the specific provider, and optionally be able to prompt the patient with more detailed questions that the provider may need to know. Since the dominant method of formatting this information today is paper forms, the system is adapted to produce a paper output of the electronic information and duplicate the paper (and electronic if applicable) forms that each provider in the community has in use. This method of producing paper forms enables the patient to fill out medical information in to the computer once and then tell the computer to complete the forms for several different providers.

The present invention provides a single point of entry for patients to enter healthcare related information in a confidential and secure fashion that is HIPAA compliant and does not interfere with physician relationships with patients or referrers. The TPS provider has no vested interest in steering patients to use one provider over another, or recommend one therapy over another so that physicians and providers can participate in the system without concern that patients will be provided conflicting information. Adoption of the system by providers is easy and does not require anything except sending in their forms. Since the output of the system of the present invention is their form filled out in a more legible format, physicians should have no problem accepting the forms.

The present invention, in one form, relates to a computer server for providing access to patient data records. The computer server includes a provider database, a patient interaction module, and a provider interaction module. The provider database has a plurality of provider patient documents, with at least one of the plurality of providers having a patient document distinct from the patient documents of the other of the plurality of providers. The patient interaction module is adapted to obtain patient specific information from a patient relating to information requested by the plurality of provider patient documents. The provider interaction module is adapted to transmit provider patient documents that include patient specific information relating to a specific patient in a format substantially identical to each of the providers.

The present invention, in another form, is a method for creating a patient and health care provider document database. First, a plurality of patient information documents is obtained from a plurality of providers. Next, the plurality of patient information documents are scanned and the patient information which is identified in the patient information documents is determined. A plurality of patient information template documents are created that include patient specific information from a patient database. Finally, a patient database is created that includes data fields for patient information common to the plurality of patient information documents.

Further aspects of the present invention involve the patient interaction module being adapted to obtain at least one of the following types of information: patient demographic, responsible party, patient insurance, patient allergies, patient medications, patient current medical problem list, patient family history, patient social history, patient vaccination history, patient chief complaint, patient history of present illness, and patient surgical history. The patient interaction module is adapted to store patient specific information in a data base file. The data base file may include fields for at least one of the following types of information: record identifying, personal identifying, patient insurance/financial, advance directives, patient health status, care documentation, care plan recommendation, and practitioners. The database file further includes extension fields for containing further information. The provider interaction module is further adapted to transmit patient scheduling messages with a provider. The provider interaction module is further adapted to transmit patient documents by one of facsimile transmission, electronic data interchange transmission, electronic mail transmission, or regular mail delivery.

Another aspect of the invention relates to a machine-readable program storage device for storing encoded instructions for a method of providing a patient information document to a health care provider according to the foregoing systems.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 4 is a flow chart diagram of the operation of the present invention relating to the process of allowing a patient to select a provider and send out their information to that provider, optionally scheduling the appointment.

FIG. 6 is a schematic relationship diagram of the correspondence of forms to providers and provider groups in the system of the present invention.

Figure 1:
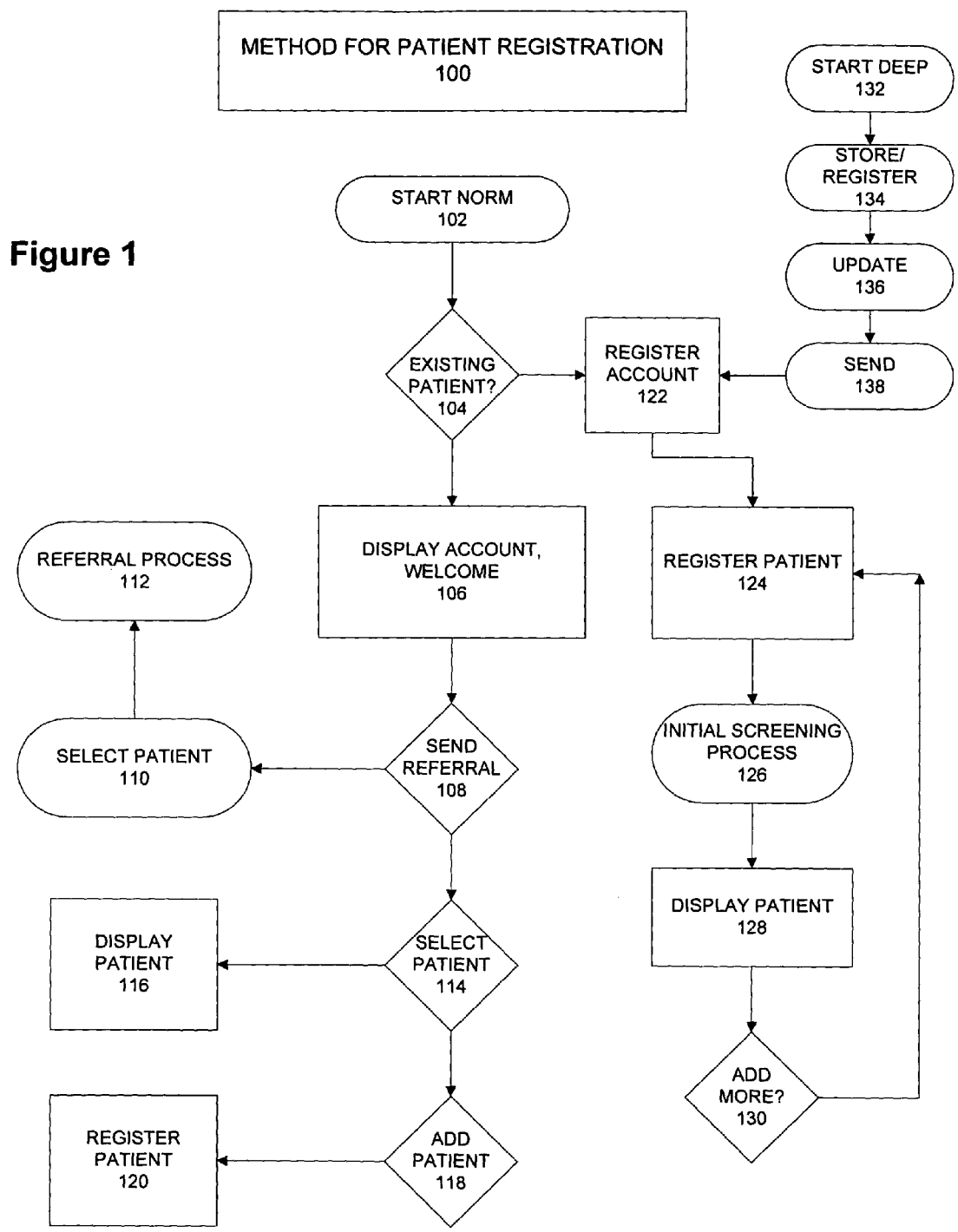
FIG. 1 is a flow chart diagram view of a patient registration process using the methodology of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DESCRIPTION OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

The detailed descriptions which follow are presented in part in terms of algorithms and symbolic representations of operations on data bits within a computer memory representing alphanumeric characters or other information. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical signals.

The present invention also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus. In particular, various general purpose machines may be used with programs written in accordance with the teachings herein, or it may prove more convenient to construct more specialized apparatus to perform the required method steps. The required structure for a variety of these machines will appear from the description below.

The present invention deals with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment.

The terms "desktop", "personal desktop facility", and "PDF" mean a specific user interface which presents a menu or display of objects with associated settings for the user associated with the desktop, personal desktop facility, or PDF. When the PDF accesses a network resource, which typically requires an application program to execute on the remote server, the PDF calls an Application Program Interface, or "API", to allow the user to provide commands to the network resource and observe any output. Although the following description details such operations in terms of a graphic user interface using icons, the present invention may be practiced with text based interfaces, or even with voice or visually activated interfaces. The term "Browser" refers to a program which is not necessarily apparent to the user, but which is responsible for transmitting messages between the PDF and the network server and for displaying and interacting with the network user. Browsers are designed to utilize a communications protocol for transmission of text and graphic information over a world wide network of computers, namely the "World Wide Web" or simply the "Web". Examples of Browsers compatible with the present invention include the Navigator program sold by Netscape Corporation and the Internet Explorer sold by Microsoft Corporation (Navigator and Internet Explorer are trademarks of their respective owners). Although the following description details such operations in terms of a graphic user interface of a Browser, the present invention may be practiced with text based interfaces, or even with voice or visually activated interfaces, that have many of the functions of a graphic based Browser.

Browsers display information which is formatted in a Standard Generalized Markup Language ("SGML") or a Hyper-Text Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a handheld device and a desktop computer either via wires or wirelessly. Synchronization ensures that the data on both the handheld device and the desktop computer are identical.

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), personal digital cellular ("PDC"), or through packet-data technology over analog systems such as cellular digital packet data (CDPD") used on the Advance Mobile Phone Service ("AMPS"). The terms "wireless application protocol" or "WAP" mean a universal specification to facilitate the delivery and presentation of web-based data on handheld and mobile devices with small user interfaces.

The system of the present invention includes both an internal and an external TPS provider module. The internal module is used for the installation and maintenance of the system for a community. In the context of the present invention, a community may be limited to a relatively small geographic area; a larger political area such as a township, county, or state; or the community may encompass the entire nation. The internal module includes software adapted to scan in the relevant forms from the community and software to develop the definition of the patient entry forms and underlying database according to a TPS model.

The internal module has scanning and forms definition software which involves: scanning the forms received from the providers (i.e., uncompleted patient screening forms); selecting portions of each of the forms with a selection tool; and interacting with a series of questions and answer definitions. The system may employ physicians or other knowledgeable users to assist in interpreting and checking the questions from the various forms and format for the answers which shall become the data for the internal module to which maintain and provide access. The results of this process include the creation of a master data entry form that obtains the majority of patient data needed by the majority of the community institutions.

The first step in the internal module is scanning the existing paper forms and having a knowledge domain expert interpret the form. The x and y coordinates of various pieces of information asked by the form is first identified along with the height and width of available space for the response. The substantive question (i.e., the screening question) is then matched to the associated x and y coordinates. There may be instances where there is no direct correlating question, in which instance that portion of the form is handled as a special case. In the course of using the internal module with several forms, there may be sufficient special cases to merit creating a new non-standard information field in the TPS model. Some forms may have alternative questions that relate to the same or similar information (for example, one form asking about lung disease and the other about COPD, a disease affecting the lungs, thus having similar but non-identical subject matter) and the knowledge domain expert needs to decide on what information field and permissible values are appropriate in the TPS model. This allows for mapping of data from information fields in the TPS model to the correct substantive response and area on a community institution form. If no relationship exists between questions, or the knowledge domain expert decides confusion may exist by combining questions, the questions would remain separate and a patient would be prompted to answer both. If a hierarchy exists, a dependency can be documented that allows the system to prompt for dependant questions only if paternal questions are answered in the affirmative. The resulting template document is defined by the coordinates of the positions (i.e., x, y, z-order, w, h, p-page) for the responses to the questions The external module includes interactive software to interact and enable a dialog with the patient to elicit the relevant patient information. In one form of the invention, a website is provided for patients to enter information. For example, the website may present dynamic questionnaires in a wizard format. The wizard format would have such checks as blocking certain questions (e.g., ask about sex) if certain information has already been entered in the patient's history (e.g., pregnancy or hysterectomy). Alternatively, the external module may include interface software that enables the retrieval of all, or a sub-set, of the relevant information from a smart card or another third party data source. The general flow of the patient registration process is shown in FIG. 1 as patient registration 100.

Patient Registration 100 typically starts at 102 with a patient visiting a health care institution. First that patient is asked if the patient is an existing patient at step 104, and if so the patient's account is displayed as a welcome screen or other appropriate indication in step 106. Next, if a referral is needed in step 108, the patient is selected in step 110 and the patient information is provided to referral process 112 (described in greater detail below). If not a referral, then select patient step 114 determines if the patient has a previously created record in the TPS system. If a record exists, it is displayed in step 116, and if not then the patient is encouraged to be added to the system in step 118, and if accepting starts the register patient step 120.

If this is not an existing patient in step 104, then the health care institution proceeds to register account 122 to initiate a patient registration on the TPS system, which begins with step 124 where the initial identification information is obtained to create the new patient record. Next some initial screening process step 126 which is described in greater detail with regards to FIG. 2. After the initial screening, the patient record is displayed in step 128, and if it is determined that more patients are to be registered in step 130, the process starts fresh at step 124.

In addition to typical patient entry starting with a patient visit to a health care institute, an alternative entry point for new patient records to the TPS system may start with step 132. There, existing electronic records are provided to be stored or registered in step 134. Such new patient records may be updated in 136 to complete information that was not immediately apparent, and finally the updated patient record is sent in step 138 into the TPS system when the health care institution next registered in step 122.

Figure 2:
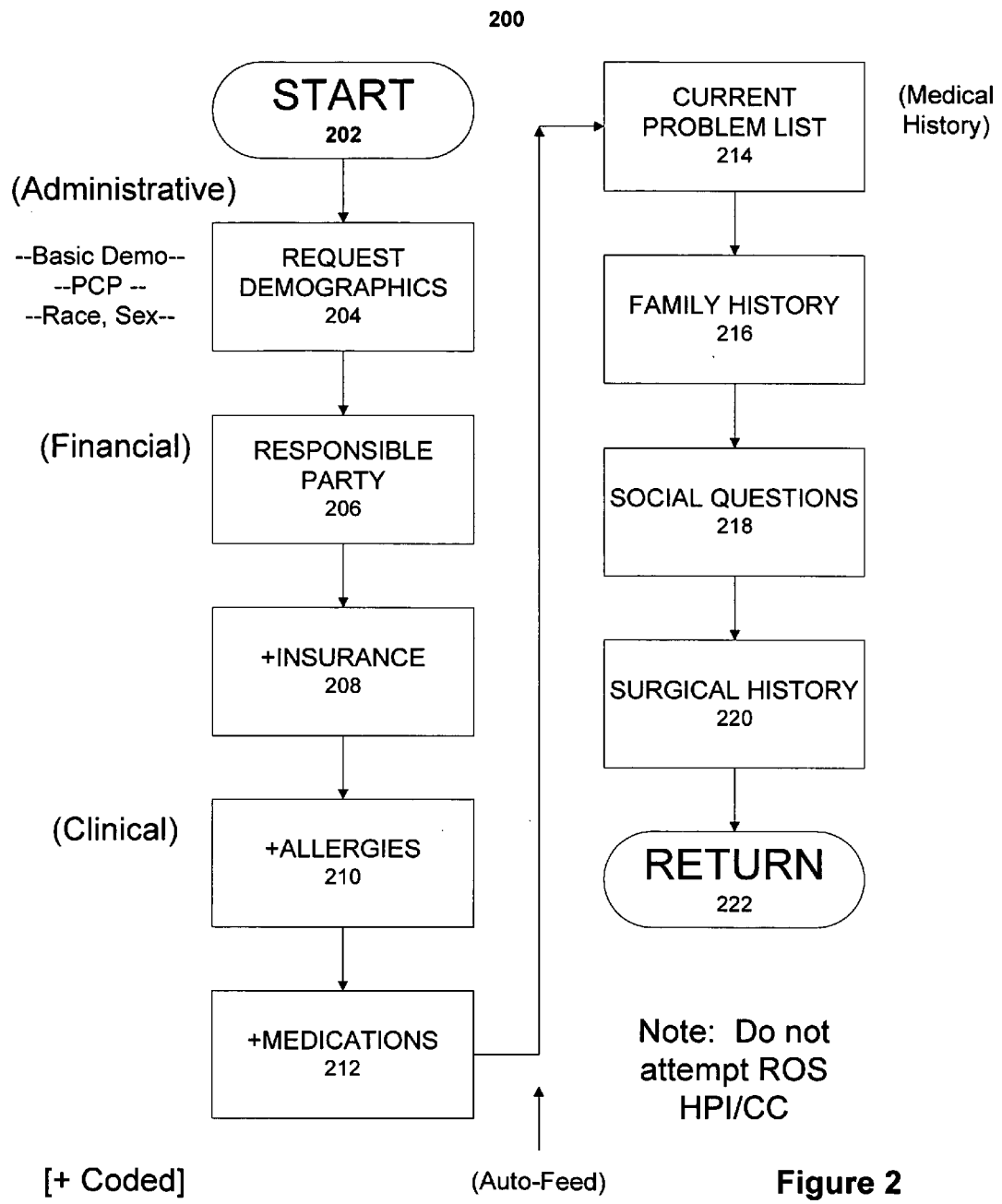
FIG. 2 is a flow chart diagram of the operation of the present invention relating to the initial screening process.

Initial Screening Process 200 of FIG. 2 starts in step 202 with obtaining the patient identifying information before obtaining information from the patient on various subjects. The steps in initial screening process 200 may be completed on paper, either by the patient or by an interview, or completed on a computer or other device. These steps may occur in many different orders, with the sequence shown in FIG. 2 being typical. Request demographics step 204 involves basic demographic information such as race and sex, and any associated primary care provider (PCP). Next, financial information such as responsible party step 206 or insurance step 208 inquire as to those subjects. Clinical questions are also typically asked such as allergies (step 210), medications (step 212), current problems (step 214), family history (step 216), social questions (step 218), and/or surgical history (step 220). Many of the clinical questions may have associated codes, some of which are universal and others which may be particular for the organization taking in the information. Once this information is collected and entered into the patient record, the results may be returned in step 222, by either printing a data sheet in the format of the health care institution or transferring an electronic record in the format of that institution.

For example, the first screen of the patient entry module may include questions on certain demographics such as name, date of birth, social security number or other identifying information, as well as portions for choosing a username and password, including confirmation screens. The wizard sections then may proceed with questions such as: (1) Are you currently taking any medications? Y/N (2) Do you have any allergies or intolerances to medication? Y/N and (3) Do you have any other allergies? Y/N. Each of these questions, if answered in the affirmative, may result in further sections that provide data entry areas for responses, using either free text and/or classified answers.

Information collected by the external module may include, but is not limited to semi-static information (e.g., name, date of birth, sex, address; insurance information such as company, policy type and identification number, policy holder, insurance card); past surgical history (including information on specific procedures, with date and location information); past and/or current pregnancies; past and/or current medical conditions (with history of conditions and onsets); current conditions (e.g., diabetic, pregnancy, etc.); family history (with relevant medical conditions, relationships, onset); social history (e.g., smoking, drinking, exercise); current medications, allergies, and intolerances (both medical and environmental); transient vitals (e.g., re-affirming or changing height, weight, etc.); and non-transient statistics and observations (e.g., blood type, disabilities, etc.). The external module may also collect dynamic information for each visit to a provider: chief complaint (i.e., the reason for the visit); review of symptoms; and allow for patients and/or providers to edit information. Information editing may include, but is not limited to, adding or discontinuing conditions (where discontinued conditions may be retained for medical history); adding or discontinuing medications (discontinue may also notify a tolerance/allergy list). Apart from visits to a provider, the external module may also allow users to maintain and/or upload: a history of where they have forwarded information and what was disclosed; lab results; views of DICOM or other image files (e.g., Xray(CR), CT, MR, PET, US images); and images of other reports.

Figure 3:
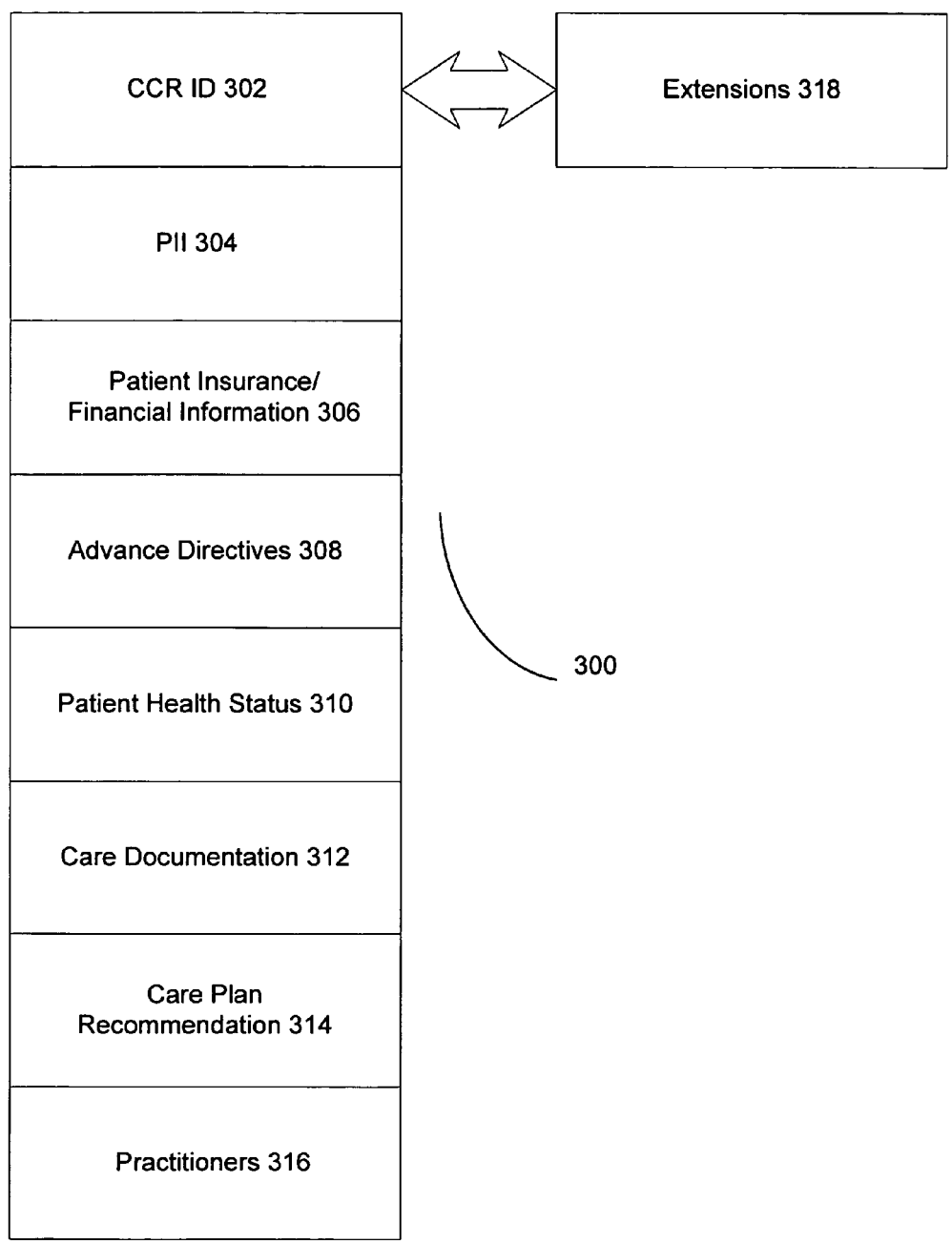
FIG. 3 is a schematic relationship diagram of a database record in accordance with one embodiment of the present invention.

The database which includes the patient information may include an object model of a patient's conditions. Such a model is schematically shown in FIG. 3. Data record 300 contains several sections that generally correspond to the American Society for Testing and Materials (ASTM) standard for the Continuity of Care Record (CCR): CCR identification fields 302, Personal Identifying Information (PII) fields 304, Patient Insurance/Financial Information fields 306, Advance Directives fields 308, Patient Health Status fields 310, Care Documentation fields 312, Care Plan Recommendation fields 314, and Practitioners fields 316. In addition to these basic fields, the CCR allows for extension fields 318 that may be associated with one or more of the defined fields or for additional information relating generally to data record 300. Extensions 318 may include fields containing information such as locally defined codes. The foregoing data record 300 may be implemented in an XML format to facilitate data rendering on various institution's forms and exchange with various computer systems including systems using the HL7 standard.

With the present invention, the TPS may recoup its investment in several distinct ways. In one form, the TPS may operate as a subscription service, assessing a service fee to each patient to maintain and distribute the patient's forms. In another form, providers may subsidizes payment or even pay the entire cost of running the system. In still another form, insurance companies may fund the system justifying the cost as avoiding problems created by disparate advice and/or incompatible treatments that occasionally result from different care providers acting on disparate information about a patient and the treatment the patient is receiving.

Access to the system may be provided through a network such as a WAN, a cellular service, or the internet. In this embodiment, a patient would first access the TPS system and create a patient account by completing basic information prior to visiting a health care provider. When the patient visits a health care provider, the provider receives the patient CCR, for example by printing out a fully or partially completed paper form by facsimile or by receiving a pre-printed form from the patient. If partially completed, the health care provider completes the remaining portions of the form and optionally updates TPS on the missing data, for example by sending an update message or by synching the data records.

In another form, access may be provided at provider locations, with patient access terminals or kiosks, where sessions are initiated at the same point where patients conventionally fill out the paper forms. Instead of the provider having to collect the paper forms and separately enter the information into a computer system, the TPS may forward a completed form to the provider by several possible routes, such as by facsimile transmission, or electronically to a printer or a computer database. Alternatively, the provider may have the patient fill out a paper form and provide the completed paper form to the TPS which may then scan in the information on the patient and populate a patient record for future visits. Providers may also enable its patients to enroll over a browser connection so that the patient may complete an information entry form before arriving at the providers' location.

One example of the flexibility afforded by the present invention relates to the referral process, show in FIG. 4 as referral process 400. The process starts at step 404 where the patient record may be obtained and updated, then a display selected in step 406 depending on the providers involved. The referring institution may have one form or format in its patient records, and the institution receiving the referral may have a different form or format. After the selection of display, additional screening may occur in step 408 to obtain the additional information desired by the institution receiving the referral. Such optional screening steps may include obtaining a chief complaint (step 410), history of present illness (HPI) details (step 412), and review of systems (ROS) information (step 414). Once the additional information for the referral receiving organization is obtained, the appointment process may commence at step 416 by simply sending a form to the receiving institution in step 418. The TPS system may additionally interact with the receiving institution in step 420 to determine if the patient already has an appointment (for example by the referring institution calling and setting up the appointment contemporaneously with the additional screening step 408). If not scheduled, then the TPS system may determine if the provider can schedule the appointment in step 422. If the provider allows TPS to schedule, then at step 424 available appointment times are queried in step 424, and available times are displayed in step 426 to allow selection of an appointment time. Upon completion of the appointment time selection, the new patient record tailored to the receiving institution is sent our in step 428. If the patient already had an appointment in step 420, the TPS system then accesses the date in step 430 and sends out the patient record tailored to the receiving institution in step 432. If the patient does not have an appointment, but the provider does not allow TPS access to schedule, then at step 422 the tailored patient record is sent out in step 432 without the appointment time.

Figure 5:
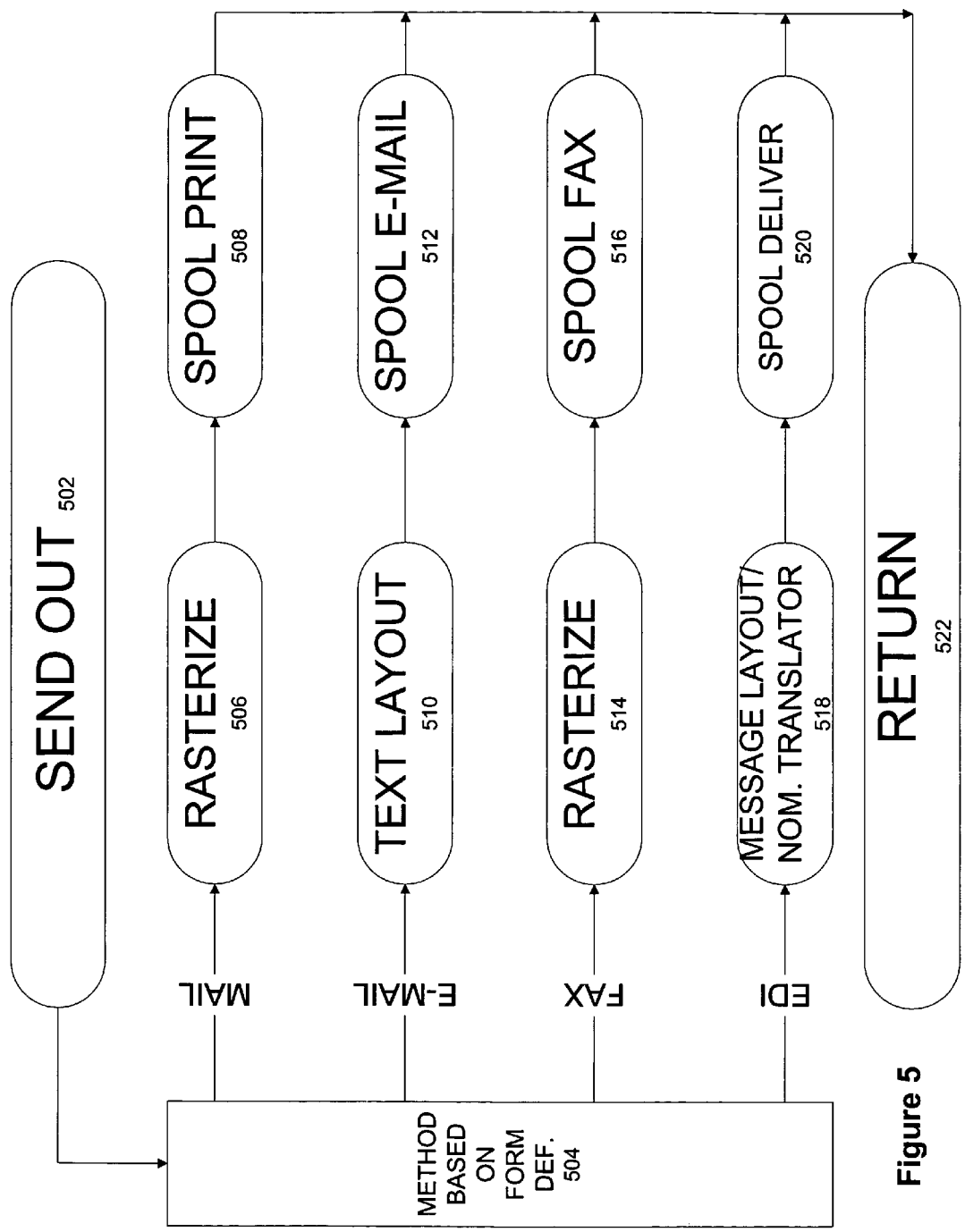
FIG. 5 is a flow chart diagram of the operation of the present invention relating to document transmission.

In the preceding examples, sending out the form to the destination organization is referenced. FIG. 5 shows more of the details of such a procedure. In send out step 502, the generation of the tailored patient record is initially sent to determine the method of delivery in step 504. If delivery is by mail, the electronic patient record is rasterized in step 506 and spooled for printing in step 508, with the rasterization corresponding to the receiving institution's existing paper forms. If delivery is by e-mail, then the electronic patient record is configured in a tailored text layout in step 510 before spooling e-mail step 512 sends the appropriate patient form out. If delivery is by facsimile, the process is similar to the mail version where rasterization step 514 is performed in correspondence to the receiving institution's existing forms and sent in spool facsimile step 516. If delivery is by electronic data interchange (EDI), then message layout and nominal translation step 518 configure the data according to the receiving institutions EDI format and is sent by spool deliver step 520. In all of these methods, a patient record is delivered to the receiving institution in a format tailored to the expectations of that receiving institution and the transmitting institution's process resumes at step 522.

FIG. 6 shows conceptually the transformation process. Form 602 may have several aliases 604, that is forms with similar data fields and information. A particular patient record may be represented by several alternative paper forms, which may have varying types and amounts of data. An alias may be a substitute form or a form in an alternative media. For example, if a patient manually enters information on the paper form of the original institution, that data may be entered by the office into an electronic alias. The TPS system may receive that information and store it in another alias of the form. Finally, each of the aliases may have corresponding forms at different institutions. The present invention maximizes data commonality and consistency while providing tailored data views for each participating institution.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A computerized method for collecting medical information from patients, the method comprising the steps of:
   receiving a plurality of substantially blank clipboard forms for collecting patient information from a plurality of health care providers, wherein the plurality of clipboard forms include a plurality of answer spaces for responding to a plurality of questions, and wherein at least a portion of the clipboard forms have distinct predefined layouts with predefined locations associated with the answer spaces;
   mapping positional coordinates of the predefined locations associated with the answer spaces for respective clipboard forms to create template documents defined by the positional coordinates of the respective clipboard forms;
   providing a database including a digitized image of the plurality of clipboard forms, respective positional coordinates of answer spaces associated with the plurality of clipboard forms based on the mapping step, and a location where respective clipboard forms should be sent when completed;
   reviewing the plurality of questions in the plurality of clipboard forms to determine a series of common questions that are substantially common to the plurality of clipboard forms;
   matching questions in the series of common questions with the positional coordinates for answer spaces associated with respective clipboard forms;
   providing a web-based system for a patient to setup an account, wherein the web-based system is configured to allow the patient to complete a patient questionnaire that includes the series of common questions;
   storing the patient's responses to the patient questionnaire on the web-based system;

allowing the selection of a healthcare provider from a plurality of healthcare providers to whom the patient's responses should be sent;

populating a clipboard form associated with the selected healthcare provider with the patient's responses based on the matching step so that the patient's responses appear in the respective answer spaces corresponding to the predefined layout for the selected healthcare provider's clipboard form; and sending the populated clipboard form to the selected healthcare provider based on the location associated with the clipboard form in the database.

2. The method of claim 1, wherein the mapping step includes a determination of x and y coordinates associated with respective answer spaces.

3. The method of claim 2, wherein the mapping step includes a determination of a height and width of respective answer spaces.

4. The method of claim 1, wherein the reviewing step includes the use of a knowledge domain expert to interpret the clipboard forms to determine where commonality in the clipboard forms exist to create the series of common questions.

5. The method of claim 1, further comprising the step of associating codes with the questions in the patient questionnaire, wherein the codes include at least one of universal codes or codes particular to the selected healthcare provider.

6. The method of claim 1, further comprising the steps of determining whether the clipboard form associated with the selected healthcare provider includes one or more specialized questions not included in the series of common questions, prompting the patient to answer any such specialized questions, and storing the patient's responses to the specialized questions on the web-based system.

7. The method of claim 6, further comprising the step of populating the clipboard form associated with the selected healthcare provider with the patient's responses to the specialized questions so that the patient's responses appear in the respective answer spaces corresponding to the predefined layout for the selected healthcare provider's clipboard form.

8. The method of claim 1, further comprising the step of selecting a patient to refer to a referral receiving organization on the web-based system, populating a clipboard form associated with the referral receiving organization with patient responses stored in the database based on the matching step so that the patient's responses appear in the respective answer spaces corresponding to the predefined layout for the referral receiving organization's clipboard form, and sending the populated clipboard form to the referral receiving organization.

9. The method of claim 8, further comprising the step of using the web-based system to schedule an appointment time for the patient with the referral receiving organization.

* * * * *